United States Patent [19]

Grollier et al.

[11] Patent Number: 4,985,955
[45] Date of Patent: Jan. 22, 1991

[54] PROCESS FOR DYEING KERATINOUS FIBRES WITH COUPLERS AND/OR "RAPID" OXIDATION DYES COMBINED WITH AN IODIDE AND DYEING COMPOSITION EMPLOYED

[75] Inventors: Jean F. Grollier, Paris; Jean Cotteret, Verneuil-sur-Seine; Didier Garoche, Levallois-Perret, all of France

[73] Assignee: L'Oreal, Paris, France

[21] Appl. No.: 198,806

[22] Filed: May 25, 1988

[30] Foreign Application Priority Data

May 25, 1987 [LU] Luxembourg .......................... 86.899

[51] Int. Cl.$^5$ ............................................... A61K 7/13
[52] U.S. Cl. ........................................ 8/406; 8/407; 8/408; 8/416; 8/421; 8/424; 8/634
[58] Field of Search .................. 8/634, 406, 407, 408, 8/416, 423, 424, 421

[56] References Cited

U.S. PATENT DOCUMENTS

| 1,677,508 | 7/1928 | Winogradoff | 8/634 |
| 4,321,054 | 3/1982 | Davis et al. | 8/634 |
| 4,324,553 | 4/1982 | Bugant et al. | 8/407 |
| 4,361,421 | 11/1982 | Bugant et al. | 8/407 |
| 4,401,435 | 8/1983 | Davis et al. | 8/627 |
| 4,420,637 | 12/1983 | Bugant et al. | 8/407 |
| 4,494,953 | 1/1985 | Bugant et al. | 8/408 |
| 4,566,875 | 1/1986 | Grollier et al. | 8/408 |
| 4,804,385 | 2/1989 | Grollier et al. | 8/423 |
| 4,808,190 | 2/1989 | Grollier et al. | 8/423 |

FOREIGN PATENT DOCUMENTS

| 0201892 | 5/1986 | European Pat. Off. . | |
| 2028818 | 6/1970 | Fed. Rep. of Germany | 8/406 |
| 2593061 | 6/1987 | France . | |
| 53-072836 | 6/1978 | Japan . | |
| 1513672 | 6/1978 | United Kingdom . | |
| 2003938 | 3/1979 | United Kingdom . | |
| 2024873 | 1/1980 | United Kingdom . | |
| 1569845 | 6/1980 | United Kingdom . | |
| 2138845 | 10/1984 | United Kingdom . | |
| 2185498 | 6/1987 | United Kingdom . | |
| 2197885 | 6/1988 | United Kingdom . | |

OTHER PUBLICATIONS

Chemical Abstracts, vol. 103, 1985, p. 679, No. 63983p, T. Perez Ruiz et al., "Oxidations of Triphenylmethane Leuco Dyes by Chloramine-T Catalyzed by Iodide, Silver, Mercury and Palladium".

Primary Examiner—Paul Lieberman
Assistant Examiner—Linda D. Skaling
Attorney, Agent, or Firm—Cushman, Darby & Cushman

[57] ABSTRACT

The invention relates to process, composition, and kit for the oxidative dyeing of keratinous fibers with couplers and/or rapid oxidation dyes combined with iodide ions.

25 Claims, No Drawings

PROCESS FOR DYEING KERATINOUS FIBRES WITH COUPLERS AND/OR "RAPID" OXIDATION DYES COMBINED WITH AN IODIDE AND DYEING COMPOSITION EMPLOYED

The present invention relates to a new process for the dyeing of keratinous fibres, especially human keratinous fibres such as hair, with oxidation dyes, and to the compositions employed in this process.

For many years, either so-called "direct" dyes, capable in themselves of coloring keratinous fibres, or so-called "oxidation" dyes which, after the development of their dyeing power in an oxidizing medium, enable a coloration to be obtained which is resistant to several treatments with shampoo, to light and to inclement weather, have been used for the dyeing of keratinous fibres, and especially hair.

Oxidation dyes are generally not dyes in themselves; they are intermediate compounds initially having little or no color, commonly referred to as "oxidation bases or precursors", which develop their dyeing power in an oxidizing medium, generally consisting of hydrogen peroxide, to give rise in a basic medium to a dye in accordance with a process, either of oxidative condensation of the oxidation dye precursor with itself, or of an oxidative condensation of the "oxidation base or dye precursor" with a compound referred to as a "color modifier" or "coupler".

The variety of molecules involved, formed by these different oxidation dyes and the possibility of coupling them, makes it possible to obtain a rich palette of colorings in respect of ashen, black, natural hues and hues with glints.

A coloration of this kind is referred to as a "permanent coloration", as opposed to the coloration obtained with the so-called "direct" dyes, which is a so-called "semi-permanent" coloration.

Processes employing a pretreatment with ions in the form of soluble salts, followed by the application of oxidation dyes after an intermediate rinsing stage, have already been proposed in the past.

The applicants have discovered, and this forms the subject of the invention, a process employing a composition containing, in combination, couplers and/or "rapid" oxidation dyes and iodide ions enabling hues to be obtained which can be different or stronger than those formerly obtained with the traditional system of oxidative polymerization of these dyes.

They also found that the colorations thereby obtained made it possible to decrease the exposure times and, in this manner, to produce a dyeing much more rapidly than with the systems of the prior art.

This process also enables hair to be dyed with dyes (couplers and/or "rapid" oxidation dyes) in an acidic medium and without employing the alkalinizing agents traditionally used in the field of oxidation dyeing, such as ammonia solution and amines, which impart an undesirable ordor to the compositions employed in the process.

A subject of the invention hence consists of a process for dyeing keratinous fibres employing a coupler and/or a "rapid" oxidation dye and an iodide in the same composition.

Another subject of the invention consists of compositions intended for use for dyeing keratinous fibres, containing a coupler and/or a "rapid" oxidation dye and an iodide.

The subject of the invention is also multi-component dyeing kits or outfits employing the compositions used in the different stages of the dyeing process.

Other subjects of the invention will become apparent on reading the description and examples which follow.

The process for dyeing keratinous fibres, preferably human, according to the invention, is essentially characterized in that at least one composition (A) containing, in a medium suitable for dyeing, by way of oxidation dyes, one or more couplers and/or one or more "rapid" oxidation dyes, in combination with iodide ions, is applied on these fibres, the application of this composition (A) being preceded or followed by the application of a composition (B) which contains, in a medium suitable for dyeing, hydrogen peroxide at a pH of between 2 and 12, and preferably between 2 and 7, and especially between 2 and 5.

The application of the compositions (A) and (B) is optionally separated by a rinsing.

According to a preferred embodiment, the composition (A) contains, either exclusively one or more couplers, or exclusively one or more "rapid" oxidation dyes, in combination with iodide ions and without the presence of other compounds capable of reacting with them, for the purpose of forming a dye by coupling.

The applicants found, in particular, that by combining, more especially, the couplers defined above with an iodide ion, it was possible, surprisingly, to obtain a permanent coloration without an oxidation base, using exclusively couplers such as, more especially, those defined below, whereas they had, hitherto, of necessity, to be used with an oxidation dye precursor.

In the process according to the invention, the iodide ion is preferably an alkali metal, alkaline earth metal or ammonium iodide, and especially potassium iodide.

The couplers, also sometimes referred to as color modifiers, are compounds known to react with oxidation bases, also referred to as oxidation dye precursors, by a process of oxidative condensation, giving colored compounds specific to the base and coupler in question. This reaction is referred to as "coupling". They are chosen from phenols, meta-diphenols, meta-aminophenols, meta-phenylenediamines, mono- or polyhydroxylated derivatives of naphthalene and of aminonaphthalene, pyrazolones and benzomorpholines.

Among couplers or color modifiers, there may be mentioned, in particular, the compounds corresponding to the formula (I):

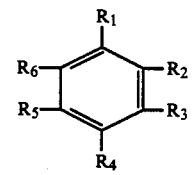

(I)

in which:

$R_1$ denotes hydroxy or an amino group which can be substituted with one or more $C_1$-$C_6$ hydroxyalkyl groups; $R_3$ and $R_5$, independently of one another, can denote hydrogen, a hydroxy group, an amino group optionally substituted with a $C_1$-$C_6$ lower hydroxyalkyl group or a $C_1$-$C_6$ lower alkyl group; and $R_2$, $R_4$ and $R_6$ can denote a hydrogen atom or a $C_1$-$C_6$ alkoxy group, a hydroxyalkoxy group or a $C_1$-$C_6$ lower alkyl group; it also being possible for R₃ and R₄ together to form a methylenedioxy group.

Among especially preferred couplers, there may be mentioned 2-methoxy-5-aminophenol, 2-methoxy-5-[N-(2-hydroxyethyl)amino]phenol, 1,3-diamino-2,6-dimethoxybenzene, 2-methoxy-1-(N-methylamino)-4-(2-hydroxyethoxy)-3-aminobenzene, 1,3-diamino-6-methoxybenzene, 1,3-diamino-4,6-dimethoxybenzene, 4,6-dimethoxy-1,3-bis[N-(2-hydroxyethyl)amino]benzene, 2,6-dimethoxy-3-[N-(2-hydroxyethyl)amino]1-aminobenzene, 2,4-dimethoxy-3-[N-(2-hydroxyethyl)amino]1-aminobenzene, 2-methyl-5-[N-(2-hydroxyethyl)amino]phenol, 1,3-bis[N-(2-hydroxyethyl)amino]-4-methoxybenzene, 3-amino-4-methoxyphenol, 3,4-methylenedioxy-1-aminobenzene, 2,6-dimethyl-3-[N-(2-hydroxyethyl)amino]phenol, 2,6dimethyl-3-aminophenol, 4-ethoxy-1-amino-3-[N,N-bis(2-hydroxyethyl)amino]benzene, (2,4-diaminophenoxy)ethanol, (2-amino-N-methyl-4-aminophenoxy)ethanol, 1-methoxy-2-[N-(2-hydroxyethyl)amino]-4-aminobenzene, 3,4-methylenedioxy-6-methoxyphenol, 3-amino-6-methylphenol, 3,4-methylenedioxy-6-methoxyaminobenzene, 3-aminophenol and 1,3-dihydroxybenzene.

Other preferred couplers are 6-aminobenzomorpholine, 1-amino-7-naphthol, 6-hydroxybenzomorpholine, 1-naphthol, 1,3-dihydroxynaphthalene and 1,2-dihydroxybenzene.

The so-called "rapid" oxidation dyes are dye precursors capable of generating colored compounds by simple oxidation in the air, during the exposure to time on the hair, that is to say generally less than 1 hour, this taking place in the absence of another oxidizing agent. They are chosen, in particular, from trihydroxylated derivatives of benzene, diaminohydroxybenzenes, aminodihydroxybenzenes, triaminobenzenes, aminohydroxybenzenes and 1,2-dihydroxybenzenes substituted on the benzene ring.

Among trihydroxylated derivatives of benzene, there may be mentioned 1,2,4-trihydroxybenzene, 1,2,4-trihydroxy-5-alkylbenzenes in which the alkyl group is a $C_1$-$C_6$ lower alkyl group and 1,2,3-trihydroxybenzene, and their salts.

Among diaminohydroxybenzenes, there may be mentioned 2,4-diaminophenol and 2,5-diamino-4-methoxy-1-hydroxybenzene, and their salts.

Among aminodihydroxybenzenes, there may be mentioned 2-amino-1,4-dihydroxybenzene, 1,4-dihydroxy-2-diethylaminobenzene and 4-aminoresorcinol, and their salts.

Among substituted 1,2-dihydroxybenzenes, 4-methyl-1,2-dihydroxybenzene and 3-methoxycatechol are especially preferred.

The aminohydroxybenzenes are chosen, in particular, from 2-amino-4-methoxyphenol, 2-aminophenol, 4,6-dimethoxy-3-amino-1-hydroxybenzene and 2,6-dimethyl-4-[N-(p-hydroxyphenyl)amino]-1-hydroxybenzene, and their salts.

By way of a triaminobenzene, there may be mentioned, 1,5-diamino-2-methyl-4-[N-(p-hydroxyphenyl)amino]benzene and its salts.

Other so-called "rapid" oxidation dyes which are usable are chosen, in particular, from brazilin, haematoxylin and alkanet extract.

These different couplers and "rapid" oxidation dyes can be used mixed or alone, in combination with iodide ions.

The subject of the invention is also dyeing compositions intended for use in a process for dyeing keratinous fibres, especially human hair, comprising, by way of an oxidation dye, exclusively one or more couplers and/or one or more so-called "rapid" oxidation dyes and iodide ions, in a medium suitable for dyeing.

A preferred embodiment consists in using, as stated above, either exclusively one or more couplers, or exclusively one or more rapid oxidation dyes. The couplers or the "rapid" oxidation dyes used in the compositions according to the invention are preferably chosen from the preferred dyes defined above.

The composition (A), containing the dye chosen from the couplers and/or "rapid" oxidation dyes and iodide ions, generally contains the dye in proportions of between 0.01 and 10% by weight relative to the total weight of the composition (A), and preferably between 0.25 and 5% by weight. The proportion of iodide in these same compositions is preferably between 0.007 and 4% by weight expressed as $I^-$ ions, and preferably between 0.08 and 1.5% by weight expressed as $I^-$ ions, relative to the total weight of the composition (A).

The hydrogen peroxide content used in the compositions (B) is generally between 1 and 40 volumes, and preferably between 2 and 20 volumes, and more especially between 3 and 10 volumes.

The ratio of the dye (coupler or "rapid" oxidation dye) to the iodide ions is preferably between 0.05 and 10, and more especially between 0.5 and 2.

The process according to the invention is carried out by arranging exposure times, for the different compositions applied in each of the different stages of the process, of between 10 seconds and 45 minutes, and preferably of the order of 2 to 25 minutes, and more especially of the order of 2 to 10 minutes.

The applicants found, in effect, that the process according to the invention made it possible to obtain colorations that were both rapid and strong, penetrating well into the fibres, and in particular human keratinous fibres such as hair, without degrading the hair shaft. These colorations also possess good resistance to washing and to light and are odorless.

They were also able to note that hair dyed several times, following regrowth, by means of the processes and the compositions employed, according to the invention, was softer and shinier and had good mechanical properties, compared with hair dyed employing the processes and compositions of the prior art.

By means of the process and the compositions according to the invention, relatively intense colorations are obtained in relatively short times, of the order of 5 to 15 minutes.

The compositions used for carrying out the process according to the invention can be presented in various forms, such as more or less thickened or gelled liquids, creams, emulsions and foams, or other forms suitable for carrying out dyeing.

The dyeing compositions intended for use in the process according to the invention, and containing the dye (coupler and/or "rapid" oxidation dye) in combination with iodide ions, generally contain an aqueous medium consisting of water and/or a water/solvent(s) mixture, the solvent(s) preferably being chosen from organic solvents such as ethyl alcohol, propyl or isopropyl alcohol, tert-butyl alcohol, ethylene glycol, ethylene glycol monomethyl, monoethyl and monobutyl ethers, ethylene glycol monoethyl ether acetate, propylene glycol, propylene glycol monomethyl ether and dipropylene glycol monomethyl ether, and methyl lactate. The especially preferred solvents are ethyl alcohol and propylene glycol.

The dyes (couplers and/or "rapid" oxidation dyes) can also be stored with the iodides in a medium consisting of anhydrous solvents, this composition being mixed at the time of use with an aqueous medium.

When the medium is aqueous, the composition (A) has a pH of between 2 and 7, and preferably between 3.5 and 7.

According to the invention, an anhydrous solvent denotes a solvent comprising less than 1% of water.

When the medium consists of a water/solvent(s) mixture, the solvents are present in concentrations preferably of between 0.5 and 75% by weight relative to the total weight of the composition, and especially between 2 and 50%, and more especially between 2 and 20%.

The compositions according to the invention can contain other adjuvants customarily used in the dyeing of keratinous fibres.

In the preferred application to the dyeing of hair, these compositions can contain, in particular, fatty amides in proportions of 0.5 to 10%, anionic, cationic, nonionic or amphoteric surfactants, or mixtures thereof, present in proportions of between 0.1 and 50% by weight, thickening agents, perfumes, sequestering agents, film-forming agents, treatment agents, dispersants, conditioners, preservatives, opacifiers, and agents that swell keratinous fibres.

The thickeners may be chosen, more especially, from sodium alginate, gum arabic, guar gum, biopolymers such as xanthan gum or scleroglucans, cellulose derivatives such as methylcellulose, hydroxyethylcellulose, hydroxypropylmethylcellulose, carboxymethylcellulose sodium salt and acrylic acid polymers. It is also possible to use inorganic thickening agents such as bentonite. These thickeners, used alone or mixed, are preferably present in proportions of between 0.1 and 5% by weight relative to the total weight of the composition, and advantageously between 0.5 and 3%.

The acidifying agents which are usable in the preferred embodiment of the process, employing the compositions at acid pH, may be chosen from lactic acid, acetic acid, tartaric acid, phosphoric acid, hydrochloric acid and citric acid.

It is also possible to adjust the pH with alkalinizing agents chosen, in particular, from amines such as alkanolamines and alkylamines, and alkali metal or ammonivium hydroxides or cabonates, in particular when the precursors are used in the form of salts of strong acids.

When the composition is used in the form of a foam, it may be packaged under pressure in an aerosol device, in the presence of a propellant and at least one foam generator. The foam generating agents can be anionic, cationic, nonionic or amphoteric foaming polymers, or surfactants of the type defined above.

For the purpose of carrying out the process according to the invention, the different compositions may be packaged in a multi-compartment device also referred to as a kit or outfit for dyeing, comprising all the components intended for application for a single dyeing on keratinous fibres, in successive applications with or without premixing. Such devices are known per se, and can comprise a first compartment containing the composition (A), containing the dye (coupler and/or "rapid" oxidation dye) in the presence of iodide ions in a medium suitable for dyeing, and, in a second compartment, a hydrogen peroxide solution.

When the medium containing the dye (coupler and/or "rapid" oxidation dye) and the iodide ions is an anhydrous medium, it is mixed, before use, with an aqueous vehicle suitable for dyeing, optionally present in a third compartment.

The composition containing the dye defined above and iodide ions in an anhydrous medium can optionally be applied directly on wet keratinous fibres.

When the medium suitable for dyeing is aqueous, the composition in the first compartment preferably possesses a pH of between 2 and 7, and especially between 3.5 and 7. The pH of the composition containing hydrogen peroxide is between 2 and 12, but it is preferably acid and between 2 and 7, and more especially between 2 and 5.

The multi-compartment devices which are usable according to the invention can be equipped with means, known per se, for mixing at the time of use, and can be packaged under an inert atmosphere.

The process and the compositions used according to the invention can be employed for dyeing hair which is natural or has already been dyed, permanent-waved or otherwise, or straightened, or hair which has been strongly or lightly bleached and optionally permanent-waved. It is also possible to use them for dyeing furs or wool.

The examples which follow are designed to illustrate the invention, without a limitation of the latter being implied.

EXAMPLE 1

90% white, permanent-waved hair is dyed by applying successively, and without rinsing between the two applications, a dyeing solution (A) of the following composition:

| | |
|---|---|
| 2-methoxy-5-aminophenol | 1.00 g |
| Potassium iodide | 1.00 g |
| Ethyl alcohol | 10.00 g |
| Water qs | 100 g |
| Citric acid qs pH = 6 | |

After 5 minutes of exposure, and without intermediate rinsing, a solution (B) of "12.5 volume" $H_2O_2$ (pH 3.7) is then applied. The hair is rinsed with water. After drying, a golden coppery light chestnut coloration is obtained.

EXAMPLE 2

90% white, permanent-waved hair is dyed by applying successively, and without rinsing between the two applications, a dyeing solution (A) of the following composition:

| | |
|---|---|
| 2,4-diaminoanisole sulphate | 2.4 g |
| Potassium iodide | 1.0 g |
| Ethyl alcohol | 5.0 g |
| Water qs | 100 g |
| Triethanolamine qs pH = 6 | |

After 5 minutes of exposure, an aqueous solution (B) of "12.5 volume" $H_2O_2$ (pH 3.7) is then applied for 5 minutes. The hair is rinsed with water. After drying, an iridescent dark ash chestnut coloration is obtained.

EXAMPLE 3

90% white natural hair is dyed by applying successively, and without rinsing between the two applications a dyeing solution (A) of the following composition:

| | |
|---|---|
| 1,3-diamino-2,6-dimethoxybenzene dihydrochloride | 2.4 g |
| Potassium iodide | 1.0 g |
| Ethyl alcohol | 5.0 g |
| Water qs | 100 g |
| Triethanolamine qs pH = 6 | |

After 5 minutes of exposure a solution (B) of "12.5 volume" $H_2O_2$ (pH 3.7) is then applied for 5 minutes. The hair is rinsed with water. After drying, a purple violet ash blond coloration is obtained.

EXAMPLE 4

90% white, natural hair is dyed by applying successively, and without rinsing between the two applications, a dyeing solution (A) of the following composition:

| | |
|---|---|
| 4-methoxy-1,3-di-N(2-hydroxyethyl)-aminobenzene dihydrochloride | 3.00 g |
| Potassium iodide | 1.00 g |
| Ethyl alcohol | 5.00 g |
| Water qs | 100 g |
| Triethanolamine qs pH = 6 | |

After 5 minutes of exposure, an aqueous solution (B) of "12.5 volume" $H_2O_2$ (pH 3.7) is then applied for 5 minutes. The hair is rinsed with water. After drying, an ash blond coloration is obtained.

EXAMPLE 5

90% white, permanent-waved hair is dyed by applying successively, and without rinsing between the two applications, a dyeing solution (A) of the following composition:

| | |
|---|---|
| 2-methoxy-1-N-methylamino-4-(2-hydroxyethyloxy)-3-aminotenzene dihydrochloride | 2.6 g |
| Potassium iodide | 1.0 g |
| Ethyl alcohol | 5.0 g |
| Water qs | 100 g |
| Triethanolamine qs pH = 6 | |

After 5 minutes of exposure, a solution (B) of "12.5 volume" $H_2O_2$ (pH 3.7) is then applied for 5 minutes. The hair is rinsed with water. After drying, a purple violet very dark grey coloration is obtained.

EXAMPLE 6

90% white, permanent-waved hair is dyed by applying successively, and without rinsing between the two applications, a solution (B) of "12.5 volume" hydrogen peroxide (pH 3.7). The exposure lasts 5 minutes. The hair is towel dried, and then the following composition (A) is applied:

| | |
|---|---|
| 6-aminobenzomorpholine | 2.3 g |
| Ammonium iodide | 1.0 g |
| Ethyl alcohol | 5.0 g |
| Water qs | 100 g |
| Triethanolamine qs pH = 6 | |

After 5 minutes of exposure, the hair is rinsed with water. After drying, an iridescent very dark ash blond coloration is obtained.

EXAMPLE 7

90% white, permanent-waved hair is dye by applying successively, and without rinsing between the two applications, a dyeing solution (A) of the following composition:

| | |
|---|---|
| 1,3-diamino-4,6-dimethoxybenzene dihydrochloride | 2.4 g |
| Potassium iodide | 1.0 g |
| Ethyl alcohol | 5.0 g |
| Water qs | 100 g |
| Triethanolamine qs pH = 6 | |

After 5 minutes of exposure, an aqueous solution (B) of "5 volumes" $H_2O_2$ (pH 3.9) is then applied for 5 minutes. The hair is rinsed with water. After drying, an iridescent chestnut color is obtained.

EXAMPLE 8

90% white, permanent-waved hair is dyed by applying successively, and without rinsing between the two applications, a dyeing solution (A) of the following composition:

| | |
|---|---|
| 2,6-dimethoxy-3-N(2-hydroxyethyl)amino-1-aminobenzene dihydrochloride | 2.9 g |
| Potassium iodide | 1.0 g |
| Ethyl alcohol | 5.0 g |
| Water qs | 100 g |
| Triethanolamine qs pH = 6 | |

After 5 minutes of exposure, an aqueous solution (B) of "12.5 volume" $H_2O_2$ (pH 3.7) is then applied for 5 minutes. The hair is rinsed with water. After drying, an iridescent coppery blond coloration is obtained.

EXAMPLE 9

90% white, natural hair is dyed by applying successively, and with rinsing between the two applications, a composition (A) as follows:

| | |
|---|---|
| 2,4-diaminoanisole sulphate | 3.0 g |
| Sodium iodide | 0.7 g |
| Ethyl alcohol | 5.0 g |
| Xanthane gum sold under the trade name RHODOPOL 23 SC by the company RHONE-POULENC | 2.0 g |
| Glycoside alkyl ether sold at 60% concentration of AS under the trade name TRITON CG 110 by the company SEPPIC | 2.1 g AS |
| Water qs | 100 g |
| Triethanolamine qs pH = 6 | |

The exposure lasts 15 minutes. The hair is rinsed with water, and then a "12.5 volume" hydrogen peroxide solution (pH 3.7) is applied while massaging the scalp for 5 minutes. After rinsing of the hair with water and drying, an iridescent, golden, natural, very dark blond coloration is obtained.

EXAMPLE 10

90% white hair is dyed by applying successively, and with rinsing between the two applications, a composition (A) as follows:

| | |
|---|---|
| 1,2,4-trihydroxy-5-methylbenzene | 1.0 g |
| Potassium iodide | 1.0 g |
| Ethyl alcohol | 10.0 g |
| Xanthane gum sold under the trade name RHODOPOL 23 SC by the company RHONE-POULENC | 2.0 g |
| Glycoside alkyl ether sold at 60% concentration of AS under the trade name TRITON CG 110 by the company SEPPIC | 2.1 g AS |
| Cationic cellulose derivative sold by the company NATIONAL STARCH under the trade name CELQUAT L 200 | 0.3 g |
| Water qs | 100 g |
| Spontaneous pH = 6 | |

The exposure last 15 minutes. The hair is rinsed with water, and then an aqueous solution (B) of "12.5 volume" hydrogen peroxide (pH 3.7) is applied while massaging the scalp for 5 minutes. After rinsing the hair with water and drying, a purple violet mahogany coloration is obtained.

EXAMPLE 11

90% white, permanent-waved hair is dyed by applying successively, and without rinsing between the two applications, a composition (A) as follows:

| | |
|---|---|
| 1,2,4-trihydroxy-5-methylbenzene | 1.4 g |
| Potassium iodide | 1.0 g |
| Ethyl alcohol | 5.0 g |
| Water qs | 100 g |
| Triethanolamine qs pH = 6 | |

The exposure lasts 5 minutes, and then a solution (B) of "12.5 volume" hydrogen peroxide (pH 3.7) is applied. After 5 minutes of exposure, rinsing with water and drying, a coppery golden blond coloration is obtained.

EXAMPLE 12

90% white, permanent-waved hair is dyed by applying successively, and without rinsing between the two applications, a composition (A) as follows:

| | |
|---|---|
| 1,2,4-trihydroxy-5-methylbenzene | 1.4 g |
| Potassium iodide | 0.1 g |
| Ethyl alcohol | 5.0 g |
| Water qs | 100 g |
| Triethanolamine qs pH = 6 | |

The exposure lasts 5 minutes, the hair is towel-dried and then a solution (B) of "5 volume" hydrogen peroxide (pH 3.9) is applied. After 5 minutes of exposure, rinsing with water and drying, a coppery golden blond coloration is obtained.

EXAMPLE 13

90% white, natural hair is dyed by applying successively, and without rinsing between the two applications, a composition (A) as follows:

| | |
|---|---|
| 1,2,4-trihydroxy-5-methylbenzene | 2.0 g |
| Potassium iodide | 1.0 g |
| Ethyl alcohol | 20.0 g |
| Water qs | 100 g |
| Triethanolamine qs pH = 4 | |

The exposure lasts 5 minutes, the hair is towel-dried and then a solution (B) of "10 volumes" hydrogen peroxide (pH 3.8) is applied. After 5 minutes of exposure, rinsing with water and drying, a very light purple violet coloration is obtained.

EXAMPLE 14

90% white, natural hair is dyed by applying successively, and without rinsing between the two applications, a solution (B) of "10 volumes" hydrogen peroxide (pH 3.8) which is left in contact for 5 minutes. The hair is towel-dried, and then the following composition (A) is applied:

| | |
|---|---|
| 1,2,4-trihydroxy-5-methylbenzene | 2.0 g |
| Potassium iodide | 1.0 g |
| Ethyl alcohol | 20.0 g |
| Water qs | 100 g |
| Triethanolamine qs pH = 4 | |

After 5 minutes of exposure, the hair is rinsed with water and after drying, an iridescent blond coloration is obtained.

EXAMPLE 15

90% white, natural hair is dyed by applying successively, and without rinsing between the two applications, a composition (A) as follows:

| | |
|---|---|
| 1,2,4-trihydroxy-5-methylbenzene | 2.0 g |
| Ammonium iodide | 1.0 g |
| Ethyl alcohol | 20.0 g |
| Xanthane gum sold under the trade name RHODOPOL 23 SC by the company RHONE-POULENC | 1.0 g |
| Glycoside alkyl ether sold at 60% concentration of AS under the trade name TRITON CG 110 by the company SEPPIC | 5.0 g AS |
| Water qs | 100 g |
| Triethanolamine qs pH = 6 | |

The scalp is massaged for 5 minutes, towel-dried, and then a solution (B) of "12.5 volume" hydrogen peroxide (pH 3.7) is applied and left in contact for 5 minutes. After rinsing with water and drying, a light purple violet coloration is obtained.

EXAMPLE 16

90% white, natural hair is dyed by applying successively, and with rinsing between the two applications, a composition (A) as follows:

| | |
|---|---|
| 1,2,4-trihydroxybenzene | 1.0 g |
| Potassium iodide | 1.0 g |
| Ethyl alcohol | 10.0 g |
| Xanthane gum sold under the trade name RHODOPOL 23 SC by the company RHONE-POULENC | 2.0 g PO-ULENC |
| Glycoside alkyl ether sold at 60% concentration of AS under the trade name | 2.1 g AS |

-continued

| | |
|---|---|
| TRITON CG 110 by the company SEPPIC | |
| Cationic cellulose derivative sold by the company NATIONAL STARCH under the trade name CELQUAT L 200 | 0.3 g |
| Water qs | 100 g |
| Spontaneous pH = 6 | |

The exposure lasts 15 minutes. The hair is rinsed with water and then a "12.5 volume" hydrogen peroxide solution (pH 3.7) is applied while massaging the scalp for 5 minutes. After rinsing the hair with water and drying, a pearlescent golden blond coloration is obtained.

EXAMPLE 17

90% white, natural hair is dyed by applying successively, and without rinsing between the two applications, a composition (A) as follows:

| | |
|---|---|
| 1,2,4-trihydroxybenzene | 1.25 g |
| Potassium iodide | 1.0 g |
| Ethyl alcohol | 5.0 g |
| Water | qs 100 g |

The exposure lasts 5 minutes. The hair is towel-dried and then a solution (B) of "5 volumes" hydrogen peroxide (pH 3.9) is applied which is left to act for 5 minutes. After rinsing with water and drying, a golden blond coloration is obtained.

EXAMPLE 18

90% white, natural hair is dyed by applying successively, and without rinsing between the two applications, a composition (A) as follows:

| | |
|---|---|
| 1,2,4-trihydroxybenzene | 1.25 g |
| Potassium iodide | 0.1 g |
| Ethyl alcohol | 5.0 g |
| Water | qs 100 g |
| Triethanolamine qs pH = 6 | |

The exposure lasts 5 minutes. The hair is towel-dried and then a solution (B) of "12.5 volume" hydrogen peroxide (pH 3.7) is applied. It is left to act for 5 minutes. The hair is rinsed with water, dried and a golden blond coloration is obtained.

EXAMPLE 19

90% white, natural hair is dyed by applying successively, and without rinsing between the two applications, a composition (A) as follows:

| | |
|---|---|
| 1,2,4-trihydroxybenzene | 4.0 g |
| Potassium iodide | 1.0 g |
| Water | qs 100 g |
| Triethanolamine qs pH = 4 | |

The exposure lasts 5 minutes. The hair is towel-dried and then a solution (B) of "10 volumes" hydrogen peroxide (pH 3.8) is applied. It is left to act for 5 minutes. The hair is rinsed with water and after drying, a golden blond coloration is obtained.

EXAMPLE 20

90% white, natural hair is dyed by applying successively, and without rinsing between the two applications, a solution (B) of "10 volumes" hydrogen peroxide. The exposure last 5 minutes. The hair is towel-dried, and then the following composition (A) is applied:

| | |
|---|---|
| 1,2,4-trihydroxybenzene | 4.0 g |
| Potassium iodide | 1.0 g |
| Water | qs 100 g |
| Triethanolamine qs pH = 4 | |

The exposure lasts 5 minutes. The hair is rinsed with water. After drying, a golden blond coloration is obtained.

EXAMPLE 21

90% white, natural hair is dyed by applying successively, and without rinsing between the two applications, a composition (A) as follows:

| | | |
|---|---|---|
| 1,2,4-trihydroxybenzene | 4.0 g | |
| Potassium iodide | 1.0 g | |
| Xanthane gum sold under the trade name RHODOPOL 23 SC by the company RHONE-POULENC | 1.0 g | |
| Glycoside alkyl ether sold at 60% concentration of AS under the trade name TRITON CG 110 by the company SEPPIC | 5.0 g | AS |
| Water | qs 100 g | |
| Triethanolamine qs pH = 6 | | |

The scalp is massaged for 5 minutes, and then towel-dried. Then a solution (B) of "12.5 volumes" hydrogen peroxide (pH 3.7) is applied, which is left to act for 5 minutes. After rinsing with water and drying, a coppery golden blond coloration is obtained.

EXAMPLE 22

90% white, permanent-waved hair is dyed by applying successively, and without rinsing between the two applications, a dyeing solution (A) of the following composition:

| | |
|---|---|
| 4-aminoresorcin hydrochlorde | 1.6 g |
| Potassium iodide | 0.1 g |
| Ethyl alcohol | 5.0 g |
| Water | qs 100 g |
| Triethanolamine qs pH = 6 | |

After 5 minutes of exposure, a solution (B) of "12.5 volumes" $H_2O_2$ (pH 3.7) is then applied for 5 minutes. The hair is rinsed with water. After drying, a dark chestnut coloration is obtained.

EXAMPLE 23

90% white, natural hair is dyed by applying successively, and without rinsing between the two applications, a dyeing solution (A) of the following composition:

| | |
|---|---|
| 4-aminoresorcin hydrochloride | 1.6 g |
| Potassium iodide | 1.0 g |
| Ethyl alcohol | 5.0 g |
| Water | qs 100 g |
| Triethanolamine qs pH = 6 | |

After 5 minutes of exposure, a solution (B) of "5 volumes" $H_2O_2$ (pH 3.9) is then applied for 5 minutes.

The hair is rinsed with water. After drying, a natural dark ash blond coloration is obtained.

EXAMPLE 24

90% white, permanent-waved hair is dyed by applying successively, and without rinsing between the two applications, a dyeing solution (A) of the following composition:

| 1,2,3 trihydroxybenzene | 1.3 g |
|---|---|
| Potassium iodide | 1.0 g |
| Ethyl alcohol | 5.0 g |
| Water | qs 100 g |
| Triethanolamine qs pH = 6 | |

After 5 minutes of exposure, a solution (B) of "12.5 volume" $H_2O_2$ (pH 3.7) is then applied for 5 minutes. The hair is rinsed with water. After drying, a coppery golden blond coloration is obtained.

EXAMPLE 25

90% white, permanent-waved hair is dyed by applying successively, and without rinsing between the two applications, a dyeing solution (A) of the following composition:

| 1,2-dihydroxybenzene | 1.1 g |
|---|---|
| Potassium iodide | 1.0 g |
| Ethyl alcohol | 5.0 g |
| Water | qs 100 g |
| Triethanolamine qs pH = 6 | |

After 5 minutes of exposure, a solution (B) of "12.5 volume" $H_2O_2$ (pH 3.7) is then applied for 5 minutes. The hair is rinsed with water. After drying, a coppery iridescent blond coloration is obtained.

EXAMPLE 26

90% white, natural hair is dyed by applying successively, and without rinsing between the two applications, a dyeing solution (A) of the following composition:

| 4-methyl-1,2-dihydroxybenzene | 1.25 g |
|---|---|
| Potassium iodide | 1.0 g |
| Ethyl alcohol | 5.0 g |
| Water | qs 100 g |
| Triethanolamine qs pH = 6 | |

After 5 minutes of exposure, a solution (B) of "12.5 volume" $H_2O_2$ (pH 3.7) is then applied for 5 minutes. The hair is rinsed with water. After drying, a pearlescent beige blond coloration is obtained.

EXAMPLE 27

90% white, natural hair is dyed by applying successively, and without rinsing between the two applications a dyeing solution (A) of the following composition:

| 2,4-diaminophenol | 1.0 g |
|---|---|
| Potassium iodide | 1.0 g |
| Ethylene glycol monoethyl ether | 10.0 g |
| Water | qs 100 g |
| Triethanolamine qs pH = 3.5 | |

After 5 minutes of exposure a solution (B) of "5 volume" $H_2O_2$ (pH 3.9) is then applied for 5 minutes. The hair is rinsed with water. After drying, a golden coppery dark blond coloration is obtained.

EXAMPLE 28

90% white, natural hair is dyed by applying successively, and with rinsing between the two applications, a dyeing solution (A) of the following composition:

| 1,2,3-trihydroxybenzene | 2.5 g |
|---|---|
| Ammonium iodide | 0.3 g |
| Ethyl alcohol | 10.0 g |
| Guar gum sold under the trade name JAGUAR HP 60 by the company CELANESE | 1.0 g |
| Glycoside alkyl ether sold at 60% concentraton of AS under the trade name TRITON CG 110 by the company SEPPIC | 5.0 g AS |
| Water | qs 100 g |
| Triethanolamne qs pH = 6 | |

The exposure lasts 15 minutes. The hair is rinsed with water and then a solution of "12.5 volume" hydrogen peroxide (pH 3.7) is applied while massaging the scalp for 5 minutes. After rinsing the hair with water and drying, a golden blond coloration is obtained.

EXAMPLE 29

90% white hair is dyed by applying successively, and without rinsing between the two applications, a solution (B) of "12.5 volume" hydrogen peroxide (pH 3.7). The exposure lasts 5 minutes. The hair is towel-dried, and then the following composition (A) is applied:

| 1,2-dihydroxybenzene | 2.0 g |
|---|---|
| Ammonum iodide | 0.5 g |
| Ethylene glycol monoethyl ether | 5.0 g |
| Water | qs 100 g |
| Triethanolamine qs pH = 6 | |

After 5 minutes of exposure, the hair is rinsed with water. After drying, an iridescent blond coloration is obtained.

EXAMPLE 30

90% white, natural hair is dyed by applying successively, and without rinsing between the two applications, a solution (B) of "12.5 volumes" hydrogen peroxide (pH 3.7). The exposure last 5 minutes. The hair is towel-dried, and the following composition (A) is applied:

| 1,2,3-trihydroxybenzene | 2.0 g |
|---|---|
| Sodium iodide | 0.7 g |
| Ethyl alcohol | 10.0 g |
| Water | qs 100 g |
| Triethanolamine qs pH = 6 | |

After 5 minutes of exposure, the hair is rinsed with water. After drying, a natural light blond coloration is obtained.

EXAMPLE 31

| 2,4-diaminoanisole sulphate | 1 g |
|---|---|
| Potassium iodide | 1 g |
| Ethyl alcohol | 10 g |
| Xanthane gum sold under the trade name RHODOPOL 23SC by the company RHONE-POULENC | 2 g |

-continued

| | |
|---|---|
| Glycoside alkyl ether sold under the trade name TRITON CG 110 by the company SEPPIC | 2.1 g AS |
| Triethanolamine qs pH 6 | |
| Water | qs 100 g |

This composition is applied for 15 minutes on 90% white, natural hair. The hair is then rinsed with water before applying for 5 minutes an aqueous solution of "20 volume" hydrogen peroxide, the pH of which has been adjusted with triethanolamine. The hair is rinsed again with water and dried. The hair is dyed in an iridescent light ash blond hue.

EXAMPLE 32

90% white, natural hair is dyed by applying in the first instance the following composition:

| | |
|---|---|
| 1,2,4-trihydroxybenzene | 2 g |
| Potassium iodide | 1 g |
| Ethyl alcohol | 10 g |
| Xanthane gum sold under the trade name RHODOPOL 23 SC by the company RHONE-POULENC | 2 g |
| Glycoside alkyl ether sold under the trade name TRITON CG 110 by the company SEPPIC | 2.1 g AS |
| Triethanolamine qs pH 6 | |
| Water | qs 100 g |

The exposure lasts 15 minutes. The hair is rinsed with water and an aqueous solution of "20 volumes" hydrogen peroxide is then applied, the pH of which has been adjusted to 8 with triethanolamine. After 5 minutes of exposure, the hair is rinsed again with water and dried. A coppery beige blond hue is obtained.

EXAMPLE 33

In the first step of a 2-step process with intermediate rinsing, there is applied on 90% white, natural hair, the following composition:

| | |
|---|---|
| 1,2,4-trihydroxybenzene | 2 g |
| 2,4-diaminoanisole sulphate | 1 g |
| Potassium iodide | 1 g |
| Ethyl alcohol | 10 g |
| Xanthane gum sold under the trade name RHODOPOL 23 SC by the company RHONE-POULENC | 2 g |
| Glycoside alkyl ether sold under the trade name TRITON CG 110 by the company SEPPIC | 2.1 g AS |
| Triethanolamine qs pH 6 | |
| Water | qs 100 g |

After 15 minutes of exposure, the hair is rinsed with water and then an aqueous solution of "20 volumes" hydrogen peroxide of pH 3 is applied for 5 minutes. After rinsing and drying, a golden coppery blond hue is obtained.

We claim:

1. A process for dyeing keratinous fibers comprising applying to said fibers at least one composition (A) comprising, in a medium suitable for dyeing said fibers, an oxidation dye, wherein said oxidation dye consists of, at least one coupler selected from the group consisting of a phenol, a metadiphenol, a meta-aminophenol, a meta-phenylenediamine, a monohydroxylated derivative of naphthalene, a polyhydroxylated derivative of naphthalene, a monohydroxylated derivative of aminonaphthalene, a polyhydroxylated derivative of aminonaphthalene, a pyrazolone and benzomorpholine, said coupler being present in an amount ranging from 0.01 to 10 percent by weight based on the total weight of said composition (A), in combination with iodide ions present in an amount ranging from 0.007 to 4 percent by weight, expressed as I$^-$ ions, relative to the total weight of said composition (A), and applying to said fibers composition (B) comprising, in a medium suitable for dyeing said fibers, hydrogen peroxide having a pH ranging from 2 to 12, the application of said composition (A) to said fibers preceding or following the application of said composition (B) to said fibers.

2. The process of claim 1 wherein said composition (B) has a pH ranging from 2 to 7.

3. The process of claim 1 wherein said iodide ions are derived from an alkali metal iodide, an alkaline earth metal iodide or ammonium iodide.

4. The process of claim 1 wherein said composition (A) containing iodides in the form of alkali metal iodides, alkaline earth metal iodides or ammonium iodides and said oxidation dye in a medium suitable for dyeing said fibers is applied to said fibers in a first stage and said composition (B) containing hydrogen peroxide in a medium suitable for dyeing said fibers is applied to said fibers in a second stage.

5. The process of claim 1 wherein said composition (B) comprises an aqueous solution of 1 to 40 volumes hydrogen peroxide.

6. The process of claim 1 wherein said composition (B) comprises an aqueous solution of 2 to 20 volumes hydrogen peroxide.

7. The process of claim 1 wherein each of said compositions (A) and (B) is applied to said fibers and is permitted to remain in contact therewith for a period of time ranging from 10 seconds to 45 minutes.

8. The process of claim 1 wherein each of said composition (A) and (B) is applied to said fibers and is permitted to remain in contact therewith for a period of time ranging from 2 minutes to 10 minutes.

9. The process of claim 1 wherein said coupler has the formula

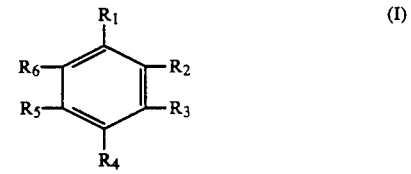

(I)

wherein
$R_1$ represents OH or an amino group unsubstituted or substituted with at least one $C_1-C_6$ hydroxyalkyl group,
$R_3$ and $R_5$, each independently, represent hydrogen, hydroxy or amino unsubstituted or substituted by $C_1-C_6$ lower alkyl or $C_1-C_6$ hydroxy lower alkyl, and
$R_2$, $R_4$ and $R_6$ represent hydrogen, $C_1-C_6$ lower alkoxy, $C_1-C_6$ lower alkyl or $C_1-C_6$ lower hydroxyalkoxy, or
$R_3$ and $R_4$ together form methylenedioxy.

10. The process of claim 1 wherein said coupler is selected from the group consisting of
2-methoxy-5-aminophenol,
2-methoxy-5-[N-(2-hydroxyethyl)]-aminophenol, 1,3-diamino-2,6-dimethoxybenzene,
2-methoxy-1-(N-methylamino)-4-(2-hydroxyethyloxy)-3-aminobenzene,
1,3-diamino-4,6-dimethoxybenzene,
1,3-diamino-6-methoxybenzene,
4,6-dimethoxy-1,3-bis[N-(2-hydroxyethyl)amino]benzene,
2,6-dimethoxy-3-[N-(2-hydroxyethyl)amino]-1-aminobenzene,
2,4-dimethoxy-3-[N-(2-hydroxyethyl)amino]-1-aminobenzene,
2-methyl-5-[N-(2-hydroxyethyl)amino]-phenol,
4-methoxy-1,3-bis[N-2-hydroxyethyl)amino]benzene,
3-amino-4-methoxyphenol,
3,4-methylenedioxy-1-aminobenzene,
2,6-dimethyl-3-[N-(2-hydroxyethyl)amino]phenol,
2,6-dimethyl-3-aminophenol,
4-ethoxy-1-amino-3-[N,N-bis(2-hydroxyethyl)amino]benzene,
(2,4-diaminophenoxy)ethanol,
[(2-amino-4-N-methylamino)phenoxy]ethanol,
1-methoxy-2-[N-(2-hydroxyethyl)amino]-4-aminobenzene,
3,4-methylenedioxy-6-methoxyphenol,
3-amino-6-methylphenol,
3,4-methylenedioxy-6-methoxyamino benzene,
3-aminophenol and
1,3-dihydroxybenzene.

11. The process of claim 1 wherein said coupler is selected from the group consisting of
6-aminobenzomorpholine,
1-amino-7-naphthol,
6-hydroxybenzomorpholine,
1-naphthol,
1,3-dihydroxynaphthalene and
1,2-dihydroxybenzene.

12. The process of claim 1 wherein said medium suitable for dyeing said fibers in said composition (A) is an aqueous medium consisting of water or a mixture of water and a solvent, and said composition (A) has a pH ranging from 2 to 7.

13. The process of claim 12 wherein said composition (A) has a pH ranging from 3.5 to 7.

14. The process of claim 12 wherein said solvent is ethyl alcohol, propyl alcohol, isopropyl alcohol, tert. butyl alcohol, ethylene glycol, ethyleneglycol monomethyl ether, ethyleneglycol monoethyl ether, ethyleneglycol monobutyl ether, ethyleneglycol monoethyl ether acetate, propylene glycol, propylene glycol monomethyl ether, dipropylene glycol monomethyl ether or methyl lactate.

15. The process of claim 1 wherein said composition (A) is a solution wherein said medium suitable for dyeing said fibers is an anhydrous solvent.

16. The process of claim 15 wherein said anhydrous solvent is ethyl alcohol, propyl alcohol, isopropyl alcohol, tert.butyl alcohol, ethyleneglycol, ethyleneglycol monomethyl ether, ethyleneglycol monoethyl ether, ethyleneglycol monobutyl ether, ethyleneglycol monoethyl ether acetate, propyleneglycol, propyleneglycol monoethyl ether, dipropyleneglycol monomethyl ether or methyl lactate.

17. The process of claim 1 wherein one or both of said compositions (A) and (B) also includes as an adjuvant at least one of a fatty amide present in an amount ranging from 0.05 to 10 weight percent; an anionic, cationic, nonionic or amphoteric surfactant, or a mixture thereof, present in an amount ranging from 0.1 to 50 weight percent; a thickening agent selected from the group consisting of sodium alginate, gum arabic, guar gum, xanthan gum, scleroglucan, methyl cellulose, hydroxyethylcellulose, hydroxypropylmethylcellulose, carboxymethylcellulose sodium salt, acrylic acid polymer and bentonite, said thickening agent being present in an amount ranging from 0.1 to 5 weight percent; a perfume; a sequestering agent; a film-forming agent; a treatment agent; a dispersant; a preservative; an opacifier; and a keratinous fiber swelling agent.

18. A keratinous fiber dyeing composition comprising in a medium suitable for dyeing said fiber, an oxidation dye wherein said oxidation dye consists of at least one coupler selected from the group consisting of a phenol, a metadiphenol, a meta-aminophenol, a meta-phenylenediamine, a monohydroxylated derivative of naphthalene, a polyhydroxylated derivative of naphthalene, a monohydroxylated derivative of aminonaphthalene, a polyhydroxylated derivative of aminonaphthalene, a pyrazolone and a benzomorpholine, said coupler being present in an amount ranging from 0.01 to 10 percent by weight based on the total weight of said composition, in combination with iodide ions present in an amount ranging from 0.007 to 4 percent by weight, expressed as $I^-$ ions, relative to the total weight of said composition.

19. The dyeing composition of claim 18 wherein said oxidation dye is present in an amount ranging from 0.25 to 5 percent by weight based on the total weight of said composition.

20. The dyeing composition of claim 18 wherein the weight ratio of said oxidation dye to said iodide ions ranges from 0.05 to 10.

21. The dyeing composition of claim 18 wherein the weight ratio of said oxidation dye to said iodide ions ranges from 0.5 to 2.

22. A kit for dyeing keratinous fibres comprising
a first compartment containing a composition (A) comprising, in a medium suitable for dyeing said fibers, an oxidation dye, wherein said oxidation dye consists of at least one coupler selected from the group consisting of a phenol, a metadiphenol, a meta-aminophenol, a meta-phenylenediamine, a monohydroxylated derivative of naphthalene, a polyhydroxylated derivative of naphthalene, a monohydroxylated derivative of aminonaphthalene, a polyhydroxylated derivative of aminonaphthalene, a pyrazolone and a benzomorpholine, said coupler being present in an amount ranging from 0.01 to 10 percent by weight based on the total weight of said composition (A), in combination with iodide ions present in an amount ranging from 0.007 to 4 percent by weight, expressed as $I^-$ ions, relative to the total weight of said compositions (A),
a second compartment containing an aqueous composition of 1 to 40 volume hydrogen peroxide at a pH ranging from 2 to 12.

23. The kit of claim 22 where in said second compartment said aqueous composition of hydrogen peroxide has a pH ranging from 2 to 7.

24. The kit of claim 22 further comprising a third compartment containing an aqueous medium suitable for dyeing said fibers for admixture with said composition (A) of said first compartment at the time of use.

25. The kit of claim 22 wherein said composition (A) is a solution wherein said medium for dyeing said fibers is an anhydrous medium.

* * * * *